United States Patent
Zhou et al.

(10) Patent No.: US 6,679,605 B2
(45) Date of Patent: Jan. 20, 2004

(54) CRYSTALLINE POLYMERIC COMPOSITIONS FOR OPHTHALMIC DEVICES

(75) Inventors: Stephen Q. Zhou, Irvine, CA (US); Christopher D. Wilcox, Mission Viejo, CA (US); Christine Liau, Irvine, CA (US); Igor Valyunin, Laguna Niguel, CA (US)

(73) Assignee: Medennium, Inc., Irvine, CA (US)

( * ) Notice: Subject to any disclaimer, the term of this patent is extended or adjusted under 35 U.S.C. 154(b) by 415 days.

(21) Appl. No.: 09/796,174

(22) Filed: Feb. 28, 2001

(65) Prior Publication Data

US 2002/0161437 A1 Oct. 31, 2002

Related U.S. Application Data

(60) Provisional application No. 60/206,197, filed on May 22, 2000.

(51) Int. Cl.[7] .................................. G02C 7/02
(52) U.S. Cl. ............. 351/159; 351/177; 623/6.56; 623/6.58; 623/907; 623/5.16
(58) Field of Search ............... 351/159, 160 R, 351/160 H, 163, 166, 167, 168, 173, 174, 175, 176, 177; 264/2.6; 606/107; 623/6.56, 6.57, 6.58, 6.59, 6.6, 6.61, 6.62, 5.11, 5.12, 5.13, 5.14, 5.15, 5.16, 906, 907, 926

(56) References Cited

U.S. PATENT DOCUMENTS

| | | | | |
|---|---|---|---|---|
| 3,691,263 A | * | 9/1972 | Stoy et al. | 351/177 |
| 4,053,442 A | * | 10/1977 | Jungr et al. | 351/160 R |
| 4,107,121 A | * | 8/1978 | Stoy | 351/160 H |
| 4,173,606 A | * | 11/1979 | Stoy et al. | 264/2.6 |
| 4,556,998 A | | 12/1985 | Siepser | 623/6 |
| 4,681,585 A | * | 7/1987 | Sayano et al. | 623/6.58 |
| 4,731,079 A | | 3/1988 | Stoy | 623/6 |
| 4,813,954 A | | 3/1989 | Siepser | 623/6 |
| 4,834,750 A | | 5/1989 | Gupta | 623/6 |
| 4,993,936 A | | 2/1991 | Siepser | 425/408 |
| 5,026,393 A | | 6/1991 | Mackool | 623/6 |
| 5,041,133 A | * | 8/1991 | Sayano et al. | 623/6.58 |
| 5,147,394 A | | 9/1992 | Siepser et al. | 623/6 |
| 5,210,111 A | | 5/1993 | Goldenberg et al. | 523/108 |
| 5,269,813 A | | 12/1993 | Yoshida et al. | 623/6 |
| 5,290,892 A | | 3/1994 | Namdaran et al. | 526/259 |
| 5,331,073 A | | 7/1994 | Weinschenk, III et al. | 526/264 |
| 5,359,021 A | | 10/1994 | Weinschenk, III et al. | 526/264 |
| 5,403,901 A | | 4/1995 | Namdaran et al. | 526/259 |
| 5,433,746 A | | 7/1995 | Namdaran et al. | 623/6 |
| 5,556,400 A | | 9/1996 | Tunis | 606/107 |
| 5,603,774 A | | 2/1997 | LeBoeuf et al. | 134/1 |
| 5,674,283 A | * | 10/1997 | Stoy | 623/5.11 |
| 5,674,960 A | | 10/1997 | Namdaran et al. | 526/259 |
| 5,693,095 A | | 12/1997 | Freeman et al. | 623/6 |
| 5,777,034 A | | 7/1998 | Shah et al. | 525/228 |
| 5,891,931 A | | 4/1999 | LeBoeuf et al. | 522/64 |
| 5,922,821 A | | 7/1999 | LeBoeuf et al. | 526/286 |
| 6,030,416 A | | 2/2000 | Huo et al. | |
| 6,234,175 B1 | | 5/2001 | Zhou et al. | |

OTHER PUBLICATIONS

USSN 09/361,729, *A Smart Ocular Plug Design and Method of Insertion for Punctal and Intracanalicular Implants*, S. Zhou, et al., filed Jul. 27, 1999; Issue Date: May 22, 2001.

Fishkind, William J., MD, *ORC MemoryLens™, A thermoplastic IOL*, Chapter 11, pp. 197–212.

* cited by examiner

*Primary Examiner*—Sang Y. Paik
*Assistant Examiner*—Fadi H. Dahbour
(74) *Attorney, Agent, or Firm*—Frost Brown Todd LLC

(57) ABSTRACT

Ophthalmic devices suitable for implantation into the eye through small incisions are disclosed. These devices are made from a composition comprising crystalline or semi-crystalline polymeric materials which have a glass transition temperature ($T_g$) of from about −100° C. to about 20° C., a melting point temperature ($T_m$) of from about 0° C. to about 37° C., and wherein $T_g$ for the material is lower than $T_m$ for the composition. Disclosed devices include intraocular lenses, corneal inlays, ocular drug delivery devices and implants for reducing intraocular pressure in glaucoma patients; intraocular lenses are preferred.

26 Claims, 10 Drawing Sheets

CRYSTALLINE POLYMERIC COMPOSITIONS FOR OPHTHALMIC DEVICES

BACKGROUND OF THE INVENTION

This application is based on and claims priority from U.S. Provisional Application No. 60/206,197, filed May 22, 2000.

Eye surgeries involving ophthalmic devices usually require an incision for introducing the ophthalmic device to the target location for their intended use. Often, it is desirable to make the incision size as small as possible for fast recovery and for minimizing potential post-operational complications and side effects. In order to understand this general small incision concept, the following examples are given for the purpose of illustration, but not to limit the scope of the present invention.

Intraocular lenses (IOLs) have been used as the replacement for the crystalline lens after cataract surgery and as a phakic lens which functions together with the intact crystalline lens for correcting refractive errors. To surgically implant an intraocular lens (IOL) or phakic lens into the eye, an incision is made on the cornea. It is desirable to keep the incision size as small as possible. Implanting a traditional polymethyl methacrylate (PMMA) IOL or a PMMA phakic lens requires an incision size of about 6 mm simply because the hard PMMA lens has an optical diameter of approximately 6 mm. In order to reduce the incision size, soft materials, such as silicone or soft acrylic material have been used for lenses. A soft lens can be folded in half and then implanted into an eye with an incision size of about 3 mm. The reduction in incision size has been proven in clinical studies to reduce surgically induced astigmatism, hasten wound healing, and reduce risk of infection and/or inflammation.

Corneal inlay is an ophthalmic device surgically implanted within the cornea. A corneal inlay is designed as a lens, about 2 to 3 mm in diameter, which provides a central nearsighted vision zone for presbyopic patients. The natural cornea surrounding the inlay provides the patient with the farsighted vision. The human cornea has a thickness of approximately 0.5 mm. To implant a thin inlay lens into the cornea, the first step is to make an incision on the corneal surface without cutting through the whole corneal layer. The second step is to make a pocket within the corneal layer with the initial incision as the pocket opening. The incision should have a sufficient width so that the artificial inlay lens can be introduced into the pocket. For example, if a hard corneal inlay lens, such as a PMMA lens, is used, the minimum incision size needs to be about the same as the diameter of the PMMA lens. As with an IOL, a deformable inlay lens allows a reduced incision size and, therefore, reduced surgical trauma.

Cytomegalovirus (CMV) infection of the retina, or CMV retinitis, usually leads to blindness if untreated. CMV retinitis progresses very rapidly, particularly in HIV patients, often within weeks. One of the treatments is to introduce an anti-CMV drug inside the eye by a slow release drug delivery device through the cornea or the sclera. To implant the drug delivery device into the eye, a small incision or hole is cut through the cornea. Then the drug delivery device is pushed through the incision or the hole. For this application, it will be ideal if the drug delivery device is a hard solid rod for easy insertion. When the drug delivery device is inside the eye, it becomes soft. In addition, if the drug delivery device can be stretched into a smaller profile, it will be implanted into a reduced incision size or hole diameter. Therefore, surgical trauma is minimized.

From the examples given above, there is a need for ophthalmic devices which can be implanted into an opening which has a size smaller than the dimension of the ophthalmic device in its intended use conditions. Furthermore, the ideal ophthalmic device is a hard solid at the time of implantation so that it can be relatively easily implanted into the soft tissue opening. In addition, when warmed by the body temperature, the "ideal" hard solid ophthalmic device can become soft and pliable for optimal tissue compatibility.

The crystalline state of polymers is defined as one that diffracts x-rays and exhibits the first order transition known as melting (L. H. Sperling, *Introduction to Physical Polymer Science,* John Wiley & Sons, New York, 1992). As in small molecules, crystallinity occurs when parts of a molecule arrange themselves in a regular order or arrangement. Unlike a small molecule, polymers that crystallize in the bulk state are never totally crystalline, a consequence of their long-chain nature and the chain entanglements. Even in homopolymers, there will be crystalline and amorphous regions. Polymers that have crystalline regions may be referred to as crystalline or semi-crystalline polymers. The development of crystallinity depends on the structure regularity in the polymer. An increase in non-regularity of the polymer structure decreases crystallinity of the polymer and results in a lower melting temperature. The increase in non-regularity may eventually prevent crystalline regions from forming.

The present invention utilizes crystalline polymers which provide a novel mechanism for deforming ophthalmic devices made from those polymers into a smaller profile than their initial size, at least in one dimension, so that they can be implanted into the eye through a relatively small incision. When the ophthalmic device is placed in the targeted location, it will return to its intended shape and dimension or adapt to a new configuration shaped by the tissue surrounding the ophthalmic device.

The present invention includes crystalline polymers that may be useful in the production of deformable lenses such as IOLs for cataract surgery, corneal inlays, and phakic refractive lenses for correcting ametropia, such as myopia, hyperopia, astigmatism, and presbyopia. The present invention also includes the use of crystalline polymers in ophthalmic devices which are not lens related. Such non-lens related devices may include, but are not limited to, ocular drug delivery devices, and implants for reducing intraocular pressure in glaucoma patients.

Stoy in his U.S. Pat. No. 4,731,079, issued Mar. 15, 1988, discloses a method of introducing and implanting an artificial intraocular lens to replace a surgically removed human crystalline lens through a small incision. The artificial lens material has a softening temperature in the range of about 0° C. to about 42° C. The method comprises the following steps: First, heat the artificial lens to a temperature higher than its softening temperature; second, deform the artificial lens into a smaller profile at least in one dimension so that it can be implanted through a small incision into the eye; third, cool down the deformed artificial lens to a temperature which is at least 5° C. less than the softening temperature, so that the artificial lens will be frozen in the deformed configuration; fourth, implant the deformed lens into the eye through a small incision. After being warmed up by the eye temperature, the deformed lens will return to its pre-deformed shape and dimension. Stoy further teaches that preferred materials include terpolymers which contain both hydrophobic and hydrophilic monomers as well as a minor amount of monomers with at least two polymerizable double bonds. These terpolymers can be hydrated due to the presence of a desirable amount of hydrophilic monomers. The plasticizer, water in the case of the terpolymer, can lower the softening temperature of the lens material. Stoy indicates that the softening temperature may correspond to the glass transition temperature ($T_g$). However, Stoy is silent on whether the softening temperature can be a melting temperature ($T_m$). Those who are skilled in the art understand that only a crystalline polymer can have a $T_m$ and that a crystalline polymer is typically not transparent due to the presence of crystalline structure. According to Stoy, one of the requirements for his invention is that the material must be highly transparent to visible light. Stoy further teaches that preferred polymers for use in his invention are amorphous, without a substantial amount of crystalline polymer phase being present.

MemoryLens™, a commercially available implantable lens, is made from the terpolymer of methyl methacrylate (MMA), hydroxyethyl methacrylate (HEMA), and a minor amount of crosslinker. According to Dr. William J. Fishkind, MemoryLens has a composition of MMA and HEMA such that the fully hydrated lens material contains approximately 20% water and has a refractive index of 1.47. At temperatures below 25° C., the copolymer is rigid and hard, while at temperatures above 25° C., the copolymer begins to soften and becomes elastic. This thermoplastic characteristic of the copolymer is a function of its glass transition temperature ($T_g$). The MemoryLens is rolled when it is soft by increasing the temperature above its $T_g$, and then hardened in a fixed and rolled configuration by cooling to temperatures below its $T_g$. This hardened rolled lens is implanted into the eye through a small incision. Once placed inside the eye, the lens starts to become soft and relaxes to resume its pre-rolled shape. The complete shape recovery may take hours to one day to finish. Dr. Fishkind has indicated that on the first postoperative day, the folding lines will have completely resolved. (William J. Fishkind, MD, Chapter 11 "ORC MemoryLens™—A thermoplastic IOL" in the book titled *Foldable Intraocular Lenses* by Robert G. Martin, James P. Gills, and Donald R. Sanders, SLACK Incorporated, 1993).

Copending U.S. patent application Ser. No. 09/361,729, filed Jul. 27, 1999, describes a punctal plug formed from a material which can be deformed to a convenient shape for insertion into the punctum, frozen into that shape, and which regains its original shape after insertion and warming. The optical characteristics of a punctal plug are not relevant to its operability. Further, no optical devices which are inserted into the eye through a hole or incision, such as intraocular lenses, are disclosed.

SUMMARY OF THE INVENTION

The present invention relates to an ophthalmic device suitable for implantation through an incision in the human eye (such as an ocular drug delivery device, an implant for reducing intraocular pressure, a corneal inlay, or, most preferably, an intraocular lens), made from a composition containing a crystalline or semi-crystalline polymeric material having the following properties:

(a) a glass transition temperature ($T_g$) in the range of from about −100° C. to about 20° C.;

(b) a melting temperature ($T_m$) in the range of from about 0° C. to about 37° C.; and (c) wherein said glass transition temperature of the polymeric material is lower than said melting temperature for the composition.

The present invention also relates to a method for implanting into the eye, through an incision, an ophthalmic device made from a composition containing a crystalline or semi-crystalline polymeric material with a $T_g$ in the range of from about −100° C. to about 20° C., and a $T_m$ in the range of from about 0° C. to about 37° C., comprising the steps of:

(a) warming up said ophthalmic device to or above its $T_m$, then deforming said ophthalmic device into a deformed shape which can be implanted through an incision where the size of said incision is smaller than said ophthalmic device in its intended use condition;

(b) cooling said deformed ophthalmic device to a temperature below the $T_m$ such that said ophthalmic device remains in said deformed shape;

(c) implanting said deformed ophthalmic device at a temperature below the $T_m$ through said incision in the eye; and (d) warming up said ophthalmic device to and above its $T_m$ by the body temperature in the eye, whereupon said ophthalmic device changes into a shape suitable for its intended use.

DETAILED DESCRIPTION OF THE INVENTION

Figure 1:
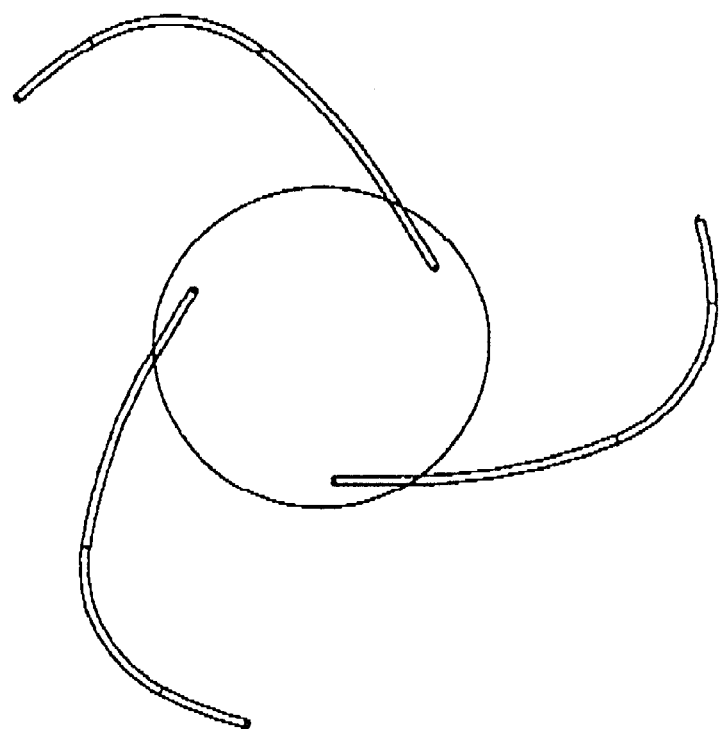
FIGS. 1–10 are top views showing examples of lens designs which may be used in the present invention.
Figure 2:
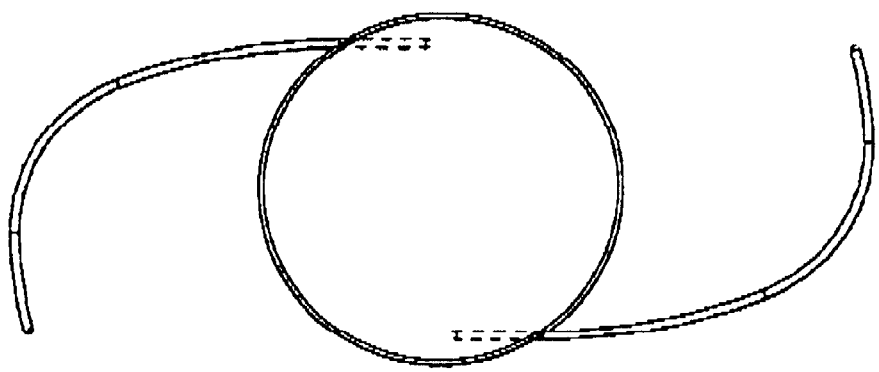
Figure 3:
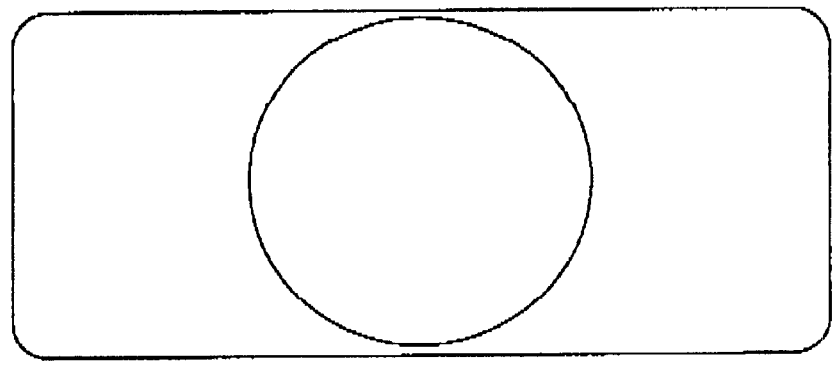
Figure 4:
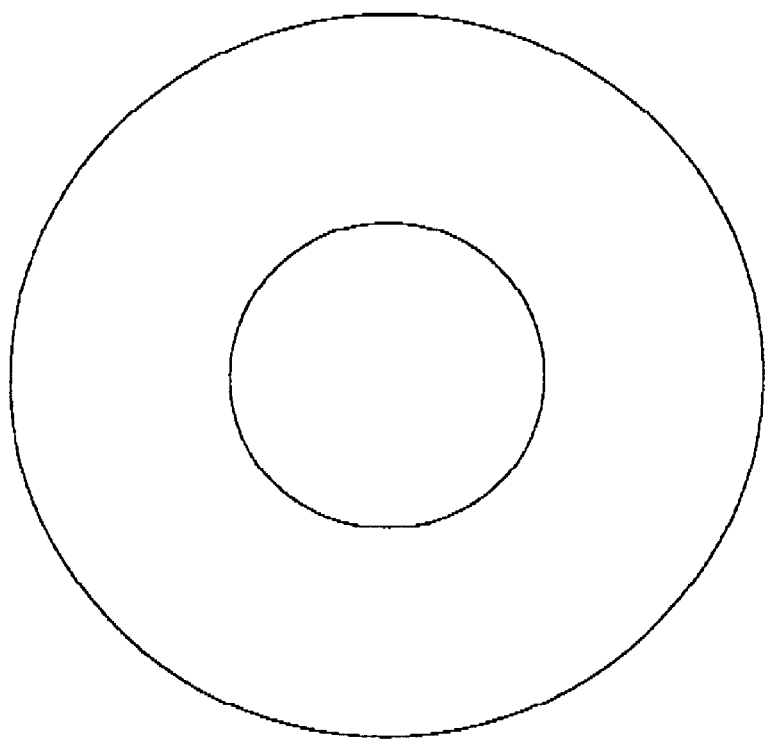

The present invention is related to ophthalmic devices and their compositions derived from crystalline polymeric materials having a crystalline melting temperature ($T_m$) in the range of about 0° C. to about 37° C., preferably in the range of about 15° C. to about 30° C. In addition to the $T_m$, these crystalline polymeric materials also have a $T_g$ (glass transition temperature) which is lower than the $T_m$ for the given composition and is in the range from about −100° C. to about 20° C., preferably in the range of about −100° C. to about −17° C. Unlike the hydrogel materials taught in the Stoy, et al. patent, discussed above, the $T_m$ and $T_g$ properties of the materials used in the present invention are not dependent on being in osmotic equilibrium in the body (i.e., $T_m$ and $T_g$ do not change in the presence of eye liquids). Although there are many different polymer structures which can form the desired crystalline regions, the preferred embodiments of the present invention include side chain crystalline-inducing polymers. The more preferred embodiments are the acrylic family polymers with long side chain alkyls (more than twelve carbons) as the crystalline-inducing groups.

It is well known to whose who are skilled in the art that as the length of the side chain of an acrylic ester monomer increases, the $T_g$ of the homopolymer decreases. For example,

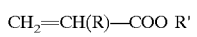

Where R=H or $CH_3$; and

R'=alkyl groups, such as $CH_3-(CH_2)_n-$, n=0 to 19.

When R=$CH_3$, and R' is the alkyl group where n increases from 0 to 17, then $T_g$ of the homopolymer of the respective monomer decreases. The trend is illustrated in Table 1. Additionally, as n increases from 11 (lauryl methacrylate) to 17 (stearyl methacrylate), side chain crystallinity starts to form. For example, polystearyl methacrylate (n=17 in R') has a side chain crystalline formation with a $T_m$ of about 36° C.

TABLE 1

Physical Properties of Methacrylate Homopolymers in Literature[1]

| n | Polymer Name | Tg (° C.) | $T_m$ (° C.) |
|---|---|---|---|
| 0 | Poly(methyl methacrylate) | 105 | N/A |
| 1 | Poly(ethyl methacrylate) | 65 | N/A |
| 3 | Poly(butyl methacrylate) | 20 | N/A |
| 11 | Poly(lauryl methacrylate) | −65 | N/A |
| 17 | Poly(stearyl methacrylate) | −100 | 36 |

Note:
[1]Herman F. Mark, et al, Encyclopedia of Polymer Science and Engineering, Volume 1, Pages 234–299, John Wiley & Sons, Inc. 1985.

The melting temperature, or $T_m$, is a characteristic of crystalline or semi-crystalline polymers. Melting may be observed visually in some materials, as the temperature increases when a material changes from white or opaque to hazy or transparent. Before the advent of sophisticated instrumental methods, melting temperatures were determined by viewing the melting polymer under a microscope between crossed polarizers. Dilatometry, where volume changes are measured, is another method for finding $T_m$. The use of a differential scanning calorimeter (DSC) is a popular method for examining the melting transition and is used for the determination of the $T_m$ in the present invention.

Polystearyl methacrylate (SMA) is a white solid polymer at room temperature in its crystalline form. However, polystearyl methacrylate is found to be transparent when it is warmed up to a temperature higher than its melting temperature and its side chain crystalline structure melts. Because polystearyl methacrylate has a $T_g$ of about −100° C., it is an elastomer after it melts. These dual thermodynamic properties, one corresponding to $T_g$ and another corresponding to $T_m$, are required for the crystalline polymers in the present invention. However, the homopolymer of stearyl methacrylate is tacky after it melts. This tackiness can be reduced by copolymerization with other monomers, such as methyl methacrylate (MMA). This tackiness can be further reduced by adding and increasing the amount of crosslinkers. Crosslinkers (for example, EGDMA, ethylene glycol dimethacrylate) can also improve the elasticity of the crystalline polymer, and therefore increase its capability for recovery from a deformed state. Table 2 is a summary of examples for the present invention.

TABLE 2

Examples for Compositions and Their Properties of the Present Invention

| No. | SMA % (by weight) | MMA % (by weight) | EGDMA % (by weight)[1] | Refractive Index (35° C.) | $T_m$ (° C.) | $T_g$ (° C.) |
|---|---|---|---|---|---|---|
| 1 | 100% | 0% | 0% | 1.470 | 34 | −100[2] |
| 2 | 95% | 5% | 0.1% | 1.470 | 26 | |
| 3[3] | 85% | 15% | 0.1% | 1.473 | 17 | |
| 4 | 80% | 20% | 0% | 1.473 | 18 | |
| 5 | 80% | 20% | 0.04% | 1.473 | 17 | |
| 6 | 60% | 40% | 0.04% | 1.477 | 10 | −17 |
| 7 | 50% | 50% | 0.04% | 1.480 | Note[4] | 17 |

Note:
[1]EGDMA is Ethylene Glycol Dimethacrylate. The percentage of EGDMA is based on 100% of monomers, i.e. (SMA + MMA)
[2]$T_g$ of −100° C. is a literature value. The literature value of $T_m$ for poly (stearyl methacrylate) is 36° C.
[3]Composition No 4 contains 1% of UV absorber, 2-(2'-hydroxy-5'-acryloxypropylenephenyl)-2H-benzotriazole
[4]$T_m$ was not observed on DSC experiments Examples of polymeric materials which may be used in the ophthalmic devices of the present invention include polymers, homopolymers, cross-linked polymers and copolymers of silicones, acrylic esters, polyurethane, hydrocarbon polymers, and combinations thereof. Specific materials include, for example, acrylic esters, copolymers of long chain methacrylates with short chain methacrylates (such as copolymers of polystearylmethacrylate with polymethylmethacrylate), and side-chain crystalizible polymers which comprise an acrylic ester of the formula:

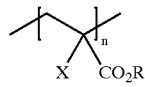

wherein X is H or a $C_1$–$C_6$ alkyl, and R is a linear $C_{10}$–$C_{26}$ alkyl.

Figure 5:
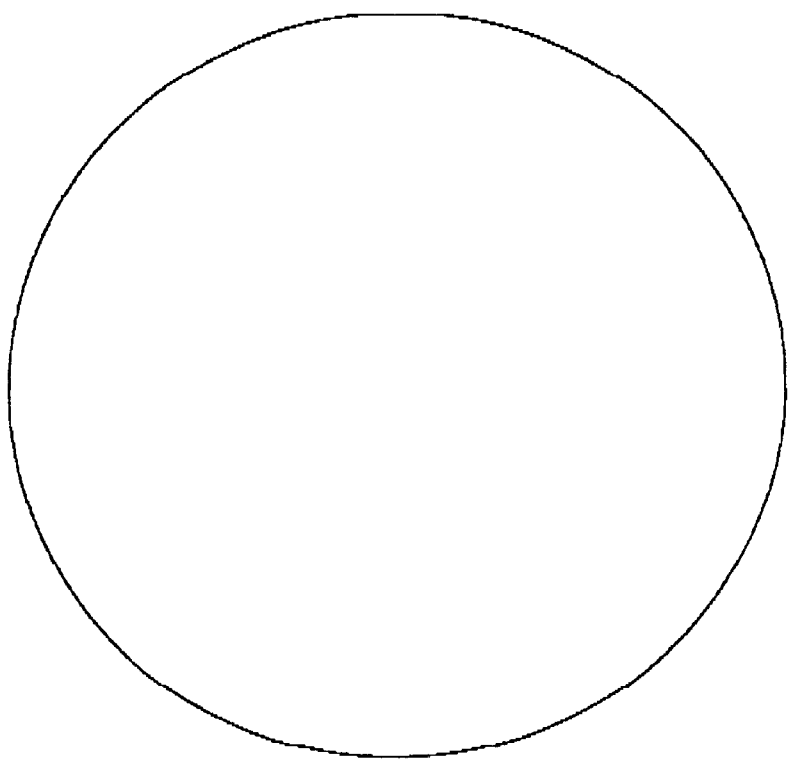
Figure 6:
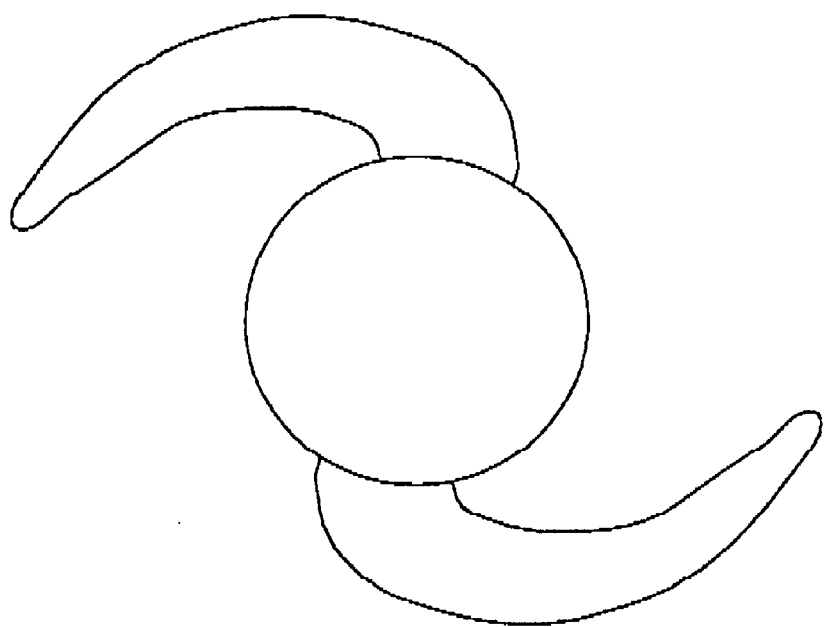
Figure 7:
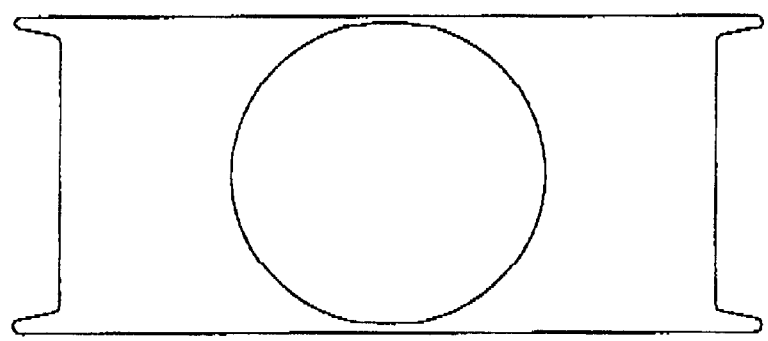
Figure 8:
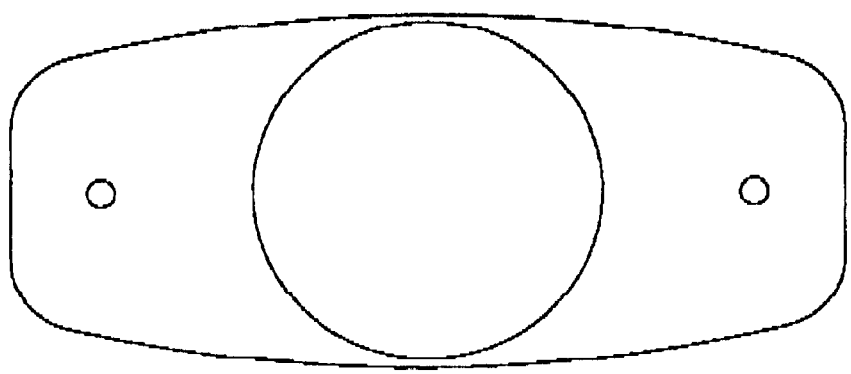
Figure 9:
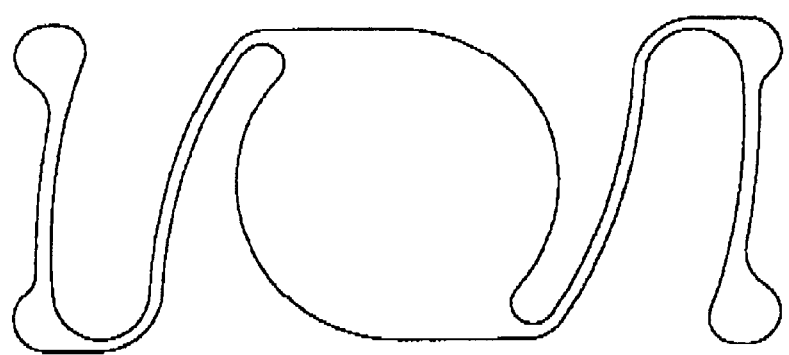
Figure 10:
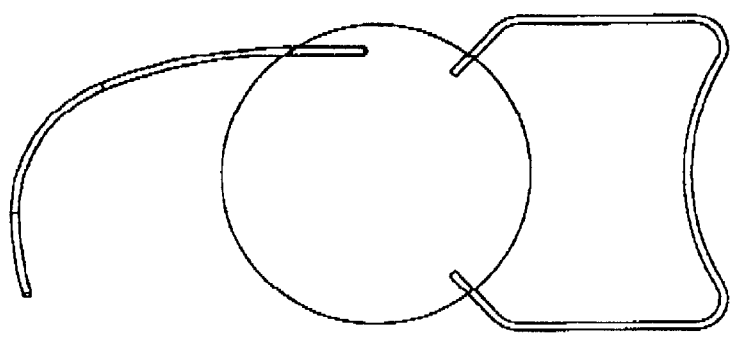

One of the applications for the present invention is to provide an alternative and superior method for implanting an IOL of various designs through a small incision. The IOL can be phakic or aphakic and it may be located in the posterior chamber of the eye or in the anterior chamber of the eye, or within the cornea, or a combination of them. Samples for the IOL design of the present invention are illustrated in, but not limited to, FIGS. 1–10. Of particular interest, is the full size lens, such as the one in FIG. 5. A full size lens has a diameter in the range from about 8 to about 11 mm and a central lens thickness in the range from about 2 to about 5 mm. The present invention can allow such a full size lens to be implanted through a small incision. Because the IOL nearly fills the whole capsular bag, it may be possible that such a fill size lens can inhibit secondary cataract formation.

One feature of the crystalline polymers used in the present invention is that they provide materials with a very wide range of properties, such as hardness (or softness) as measured by Durometers. Because $T_g$ and $T_m$ are two distinctly different thermodynamic transitions in polymer properties, it is possible to provide very soft materials by the present invention. For instance, example 1 in Table 2 has a melting point of 34° C. corresponding to the crystalline structure formed by the side chain stearyl group, and a $T_g$ of −100° C. corresponding mainly to the long polymeric backbone structure. At room temperature, it is a hard white solid. However, when the copolymer is heated up to the melting temperature or higher, it becomes transparent after all crystalline side chains have melted. It also becomes very soft because the melted side chain stearyl groups function as a plasticizer or as if it were a "solvent". This low hardness can be a very useful property in the case of a full size lens design which may possibly restore accommodation for the presbyopia patients.

The "fluid" property due to the melted crystalline side chain is also the driving force in the present invention for the ophthalmic device to adapt to a new configuration shaped by the surrounding tissue. On the other hand, the elasticity due to the long chain of the polymer backbone and the crosslinking is the driving force for the shape recovery of the ophthalmic devices from the deformed shape to the pre-deformed shape. This crystalline—fluid interphase change of the long side chain provides a novel mechanism for achieving the goals of the present invention.

In order to understand the way the present invention is practiced, an intraocular lens (IOL) is used as an example. The IOL of the present invention is made from crystalline polymeric materials having the following properties:

(1) Crystalline melting temperature, $T_m$, in the range from about 0° C. to about 37° C., preferably from about 15° C. to about 30° C.

(2) Glass transition temperature, $T_g$, in the range from about -100° C. to about 20° C., preferably from about -100° C. to about -17° C. In all cases, $T_g$ should not be higher than room temperature.

(3) Being optically transparent at or above the $T_m$. On the other hand, it is not necessary for the IOL made from the crystalline polymeric material to be transparent below the $T_m$. It may not be a requirement for non-lens related applications that the crystalline polymer be transparent at any given temperature. Furthermore, other additives may be added to the crystalline polymer composition as required by the specific circumstances. For example, an ultraviolet (UV) absorber may be incorporated into lenses for the protection of human eyes from damage caused by UV light exposure. Another example is that barium sulfate may be added to a non-lens device for rendering it radio-opaque. Therefore, the device can be examined by a radiological method if needed.

The method for implanting the IOL (or other ophthalmic device) of the present invention includes the following steps:

(a) Warm the IOL to a temperature at or above the $T_m$, then deform the IOL into a shape, such as folded, rolled, and/or stretched at the same time, which can be implanted through a small incision into the eye. The ideal size for the incision is from about 2 to about 4 mm.

(b) Cool down the deformed IOL to a temperature below the $T_m$ while the deforming force, such as folding, rolling, clamping, and/or stretching, etc., is still applied to the IOL. After removing the deforming force, the cooled IOL will remain in its deformed shape.

(c) Implant the deformed lens at a temperature below the $T_m$ through a small incision into the eye so that the lens remains in the solid deformed form and that it is relatively easy to insert into the soft tissue opening.

(d) When warmed up to and above the $T_m$ by the body temperature of the eye, the deformed IOL will return to its pre-deformed shape, providing the desirable optical power and resolution for the patient.

EXAMPLES

Example 1

Lens Preparation

To a round-bottomed flask, equipped with a magnetic stirring bar, is added a mixture of 4.75 grams of SMA, 0.25 gram of MMA, 5 microliters of ethylene glycol dimethacrylate, and 0.01 gram of benzoyl peroxide. The flask is purged with nitrogen gas for about 2 minutes and subsequently maintained under positive nitrogen atmosphere. The reaction mixture is then heated to about 110° C. in a silicone oil bath while stirring. After approximately 5 minutes, evolving of gas is observed, indicating decomposition of the benzoyl peroxide initiator to form benzoyloxy radicals initiating the polymerization reaction. After approximately 5 minutes from when the initial gas evolution is first observed, the reaction mixture becomes obviously viscous, indicating the polymerization and crosslinking reaction has occurred. Before the reaction mixture becomes too viscous to be poured out from the flask, a small amount of the mixture is taken out with a spatula and is transferred into an IOL mold. The mold is then closed and is placed into a preheated oven at 110° C. for 16 hours. After the mold is taken out from the oven and cools down to the room temperature, the mold is placed in a refrigerator for about 2 hours. The mold is then opened. A white or translucent solid IOL is carefully removed from the mold.

The IOL prepared from above procedure is placed in warm water (37° C., for example), and the IOL gradually changes from the white or translucent solid to a transparent soft lens. This soft lens can be stretched to reduce the intersectional area in the warm water bath. The stretched IOL is then removed from the warm water bath and allowed to cool down to the room temperature. The stretched IOL retains its stretched shape after about 3 minutes. The stretched IOL gradually changes from transparent to translucent and then to white hard solid. If an ice water bath is used instead of room temperature air, this "freezing" process can be completed in about 1 minute.

When the stretched IOL is warmed again in a 37° C. saline solution or water bath, it returns to its pre-stretched shape in about 1 minute. The recovered lens is transparent and soft as long as the temperature is maintained at 37° C. or higher.

Other compositions in Table 2 are prepared in a similar manner. When a UV absorber is used, it can be added to the initial reaction mixture before the heating step. In addition, ice water is preferably used for these compositions with the $T_m$ less than 20° C. for the freezing step.

Example 2

Rod Preparation

A mixture of 5 grams of stearyl methacrylate and 0.01 gram of benzoyl peroxide is warmed to about 40° C. so that it becomes a homogenous solution. The mixture is degassed and refilled with nitrogen. After the mixture is transferred into a polypropylene tube with an internal diameter of about 1 mm and with one end pre-sealed by heating, the open end is also sealed by heating. The sealed tube is about 2 inches long and is placed in an oven at 110° C. for 16 hours. At the end of the reaction, the oven is cooled down to room temperature. Then both ends of the sealed tube are cut off with a razor. The white solid rod inside the tube can be pushed out from the tube with a metal wire.

The white solid rod prepared from above procedure can be warmed up in water bath (45° C. for example). It becomes transparent and soft almost instantly. The soft rod is stretched in the water bath until the diameter of the rod becomes about 0.3 mm. The stretched rod is then lifted from the warm water bath to the room temperature air. It becomes solid in about 1 minute and retains its stretched shape as long as the temperature remains below its melting temperature.

When the stretched rod is warmed up in a saline solution, such as 37° C., it becomes soft and its diameter changes back to 1 mm in about 1 minute.

What is claimed is:

1. An ophthalmic device suitable for implantation through an incision in the human eye, selected from intraocular lenses, corneal inlays, ocular drug delivery devices, and implants for reducing intraocular pressure, made from a composition containing a crystalline or a semi-crystalline polymeric material having the following properties:

(a) a glass transition temperature ($T_g$) in the range from about -100° C. to about 20° C.;

(b) a melting temperature ($T_m$) in the range from about 0° C. to about 37° C.; and (c) wherein said glass transition temperature ($T_g$) of the polymeric material is lower than said melting temperature ($T_m$) for the composition.

2. The ophthalmic device of claim 1 in the form of an intraocular lens.

3. The ophthalmic device of claim 2 wherein said intraocular lens is a full size lens.

4. The ophthalmic device of claim 3 wherein said full size lens has a diameter of from about 8 to about 11 mm and central lens thickness of from about 2 to about 5 mm.

5. The ophthalmic device of claim 3 wherein said full size lens is an accommodative lens.

6. The ophthalmic device of claim 2 wherein the polymeric material is optically transparent at or above $T_m$.

7. The ophthalmic device of claim 6 wherein the polymeric material has a $T_m$ of from about 15° C. to about 30° C.

8. The ophthalmic device of claim 2 wherein the polymeric material has a $T_g$ of from about −100° C. to about −17° C.

9. The ophthalmic device of claim 1 wherein the polymeric material is selected from polymers, homopolymers, cross-linked polymers and copolymers of silicones, acrylic esters, polyurethane, hydrocarbon polymers, and combinations thereof.

10. The ophthalmic device of claim 1 wherein the polymeric material is an acrylic ester.

11. The ophthalmic device of claim 10 wherein the polymeric material is a copolymer of polystearylmethacrylate and polymethyl methacrylate.

12. The ophthalmic device of claim 10 wherein the polymeric material is a side-chain crystallizable polymer which comprises an acrylic ester of the formula:

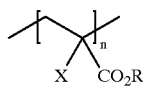

wherein X is H or a $C_1$–$C_6$ alkyl; and R is a linear $C_{10}$–$C_{26}$ alkyl.

13. A method for implantation through an incision in the eye of an ophthalmic device made from a composition containing a crystalline or a semi-crystalline polymeric material with a $T_g$ in the range from about −100° C. to about 20° C. and a $T_m$ in the range from about 0° C. to about 37° C., comprising the steps of:
 (a) warming up said ophthalmic device to or above its $T_m$, then deforming said ophthalmic device into a deformed shape which can be implanted through an incision where the size of said incision is smaller than the said ophthalmic device in its intended use condition;
 (b) cooling down said deformed ophthalmic device to a temperature below the $T_m$, such that said ophthalmic device remains in said deformed shape;
 (c) implanting said deformed ophthalmic device at a temperature below the $T_m$ through said incision in the eye; and
 (d) warming up said ophthalmic device to and above its $T_m$ by the body temperature of the eye, whereupon said ophthalmic device changes into a shape suitable for its intended use.

14. The method according to claim 13 wherein the ophthalmic device is selected from intraocular lenses, corneal inlays, ocular drug delivery devices, and implants for reducing intraocular pressure.

15. The method according to claim 14 wherein the ophthalmic device is an intraocular lens.

16. The method according to claim 15 wherein said intraocular lens is a full size lens.

17. The method according to claim 16 wherein said full size lens has a diameter of from about 8 to about 11 mm and central lens thickness of from about 2 to about 5 mm.

18. The method according to claim 16 wherein said full size lens is an accommodative lens.

19. The method according to claim 15 wherein the length of the incision is from about 2 to about 4 mm.

20. The method according to claim 15 wherein the polymeric material is optically transparent at or above $T_m$.

21. The method according to claim 20 wherein the polymeric material has a $T_m$ of from about 15° C. to about 30° C.

22. The method according to claim 21 wherein the polymeric material has a $T_g$ of from about −100° C. to about −17° C.

23. The method according to claim 14 wherein the polymeric material is selected from polymers, homopolymers, cross-linked polymers and copolymers of silicones, acrylic esters, polyurethane, hydrocarbon polymers, and combinations thereof.

24. The method according to claim 23 wherein the polymeric material is an acrylic ester.

25. The method according to claim 24 wherein the polymeric material is a copolymer of polystearylmethacrylate and polymethylmethacrylate.

26. The method according to claim 24 wherein the polymeric material is a side-chain crystallizable polymer which comprises an acrylic ester of the formula:

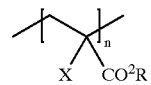

wherein X is H or a $C_1$–$C_6$ alkyl; and R is a linear $C_{10}$–$C_{26}$ alkyl.

* * * * *

UNITED STATES PATENT AND TRADEMARK OFFICE
CERTIFICATE OF CORRECTION

PATENT NO. : 6,679,605 B2
DATED : January 20, 2004
INVENTOR(S) : Stephen Q. Zhou et al.

It is certified that error appears in the above-identified patent and that said Letters Patent is hereby corrected as shown below:

<u>Column 9,</u>
Line 1, please change "...device of claim 2 wherein..." to
-- ...device of claim 7 wherein... --.

Signed and Sealed this

Eighteenth Day of May, 2004

JON W. DUDAS
*Acting Director of the United States Patent and Trademark Office*